United States Patent [19]

Davies

[11] Patent Number: 4,794,322

[45] Date of Patent: Dec. 27, 1988

[54] METHOD, SYSTEM, AND TOOL FOR INVESTIGATING BOREHOLE CASINGS

[75] Inventor: Dylan Davies, Tokyo, Japan

[73] Assignee: Schlumberger Technology Corp., New York, N.Y.

[21] Appl. No.: 925,035

[22] Filed: Oct. 30, 1986

[30] Foreign Application Priority Data

Nov. 1, 1985 [JP] Japan ............................ 60-244217

[51] Int. Cl.$^4$ .......................................... G01R 27/02
[52] U.S. Cl. .............................. 324/65 CR; 324/65 R
[58] Field of Search .............. 324/65 R, 65 P, 65 CR, 324/64, 71.2, 347–349, 351, 368

[56] References Cited

U.S. PATENT DOCUMENTS

| | | | |
|---|---|---|---|
| 2,371,658 | 3/1945 | Stewart | 175/182 |
| 2,459,196 | 1/1949 | Stewart | 175/182 |
| 2,553,350 | 3/1951 | Bayhi | 175/183 |
| 3,548,362 | 12/1970 | Blank | 339/95 |
| 4,431,963 | 2/1984 | Walkow | 324/65 R |
| 4,431,964 | 2/1984 | Walkow | 324/65 R |

OTHER PUBLICATIONS

Aguilar, J. R. "Redisenan Medidor de Potencial", *Petroleo Int.*, Jan. 1976, pp. 33–36.

Aguilar, J. R. "Diseno y Aplicacion de un Dispositivo de Registro de Potencial Diferencial Para Estudio de Fugas de Corriente o Interferencia Exterior en Tuberias de Revestimiento en Pozos Petroleros", *Ingenieria Petrolera*, Apr. 1975, pp. 159–171.

Kirklen, C. A., "Evaluation and Design Considerations for Cathodic Protection of Well Casings", Proceedings of 17th Annual Appalachian Underground Corrosion Short Course, *Engineering Experiment Station Bulletin*, No. 106, 1972, pp. 545–554.

Primary Examiner—M. H. Paschall
Assistant Examiner—A. Jonathan Wysocki
Attorney, Agent, or Firm—David P. Gordon; Peter Y. Lee; Keith G. W. Smith

[57] ABSTRACT

Systems, for investigating casings which are fitted into boreholes that traverse earth formations and which are suitable for use in evaluating and/or optimizing the cathodic protection of casings and for finding the location and rate of casing corrosion, generally includes a downhole tool capable of investigating the casing along a measurement control unit located around the surface of the earth formation, and a cable having one end connected to the downhole tool and the other connected to the measurement control unit, with the cable including at least a plurality of first connection lines. The tool invention generally includes at least a first pair of longitudinally spaced electrodes, at least a pair of second connection lines, each of the second connection lines having one end connected to a corresponding one of the electrodes, and relays interposed between the first connection lines and the second connection lines. The relays are arranged such that in a first position, the first connection lines of the cable are short-circuited, and in a second position, the first connection lines are connected to their corresponding second connection lines thereby establishing an electrical connection between the measurement control unit and the electrodes. Accurate corrected high resolution potential difference and casing resistance measurements are so obtained. Likewise, contact resistance measurements can be made and used to perform a quality control screening of the other measurements.

27 Claims, 8 Drawing Sheets

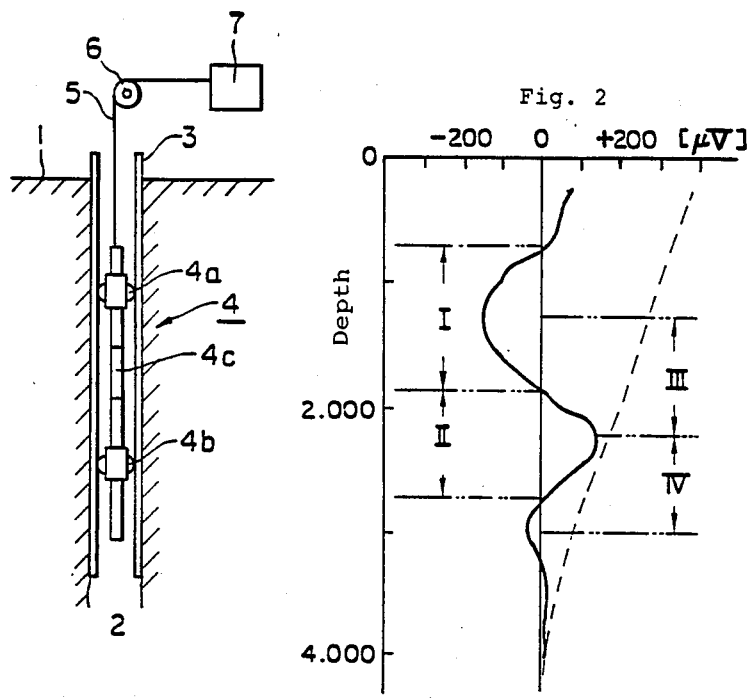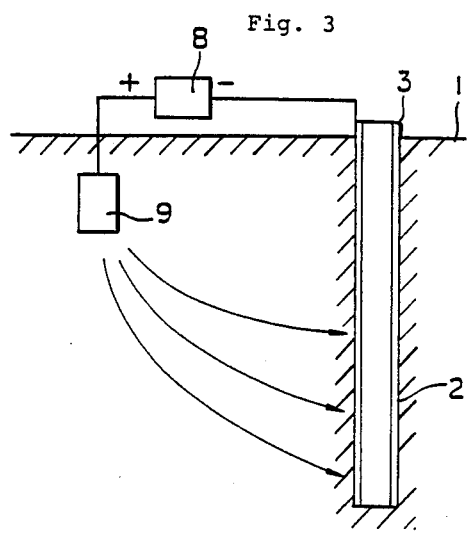

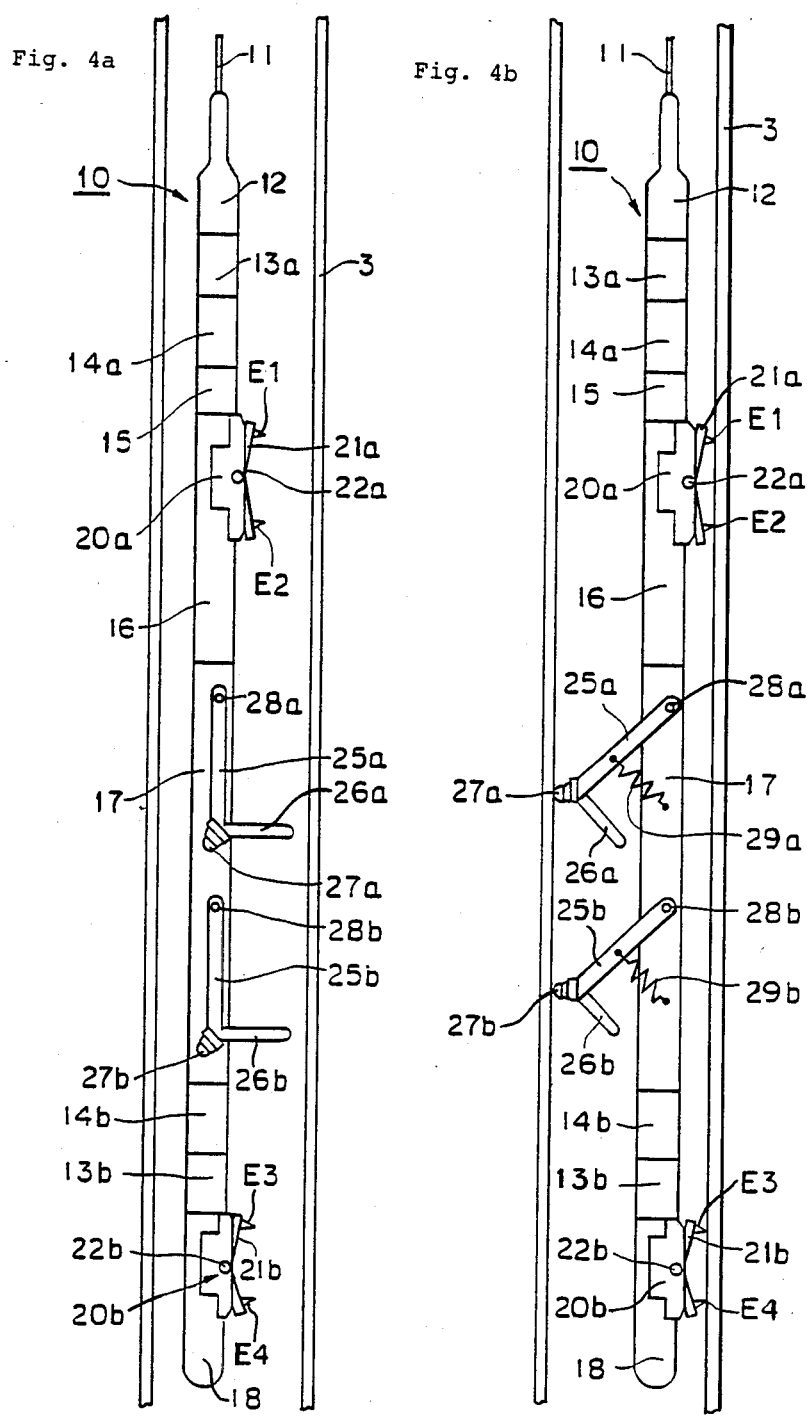

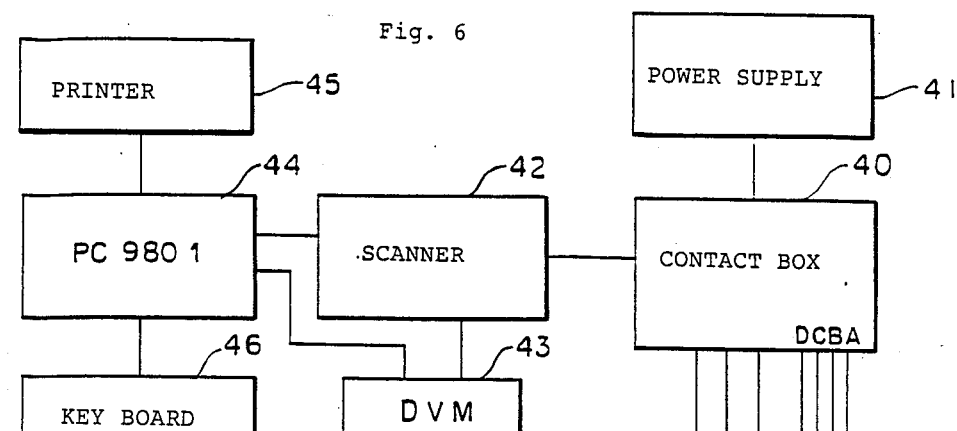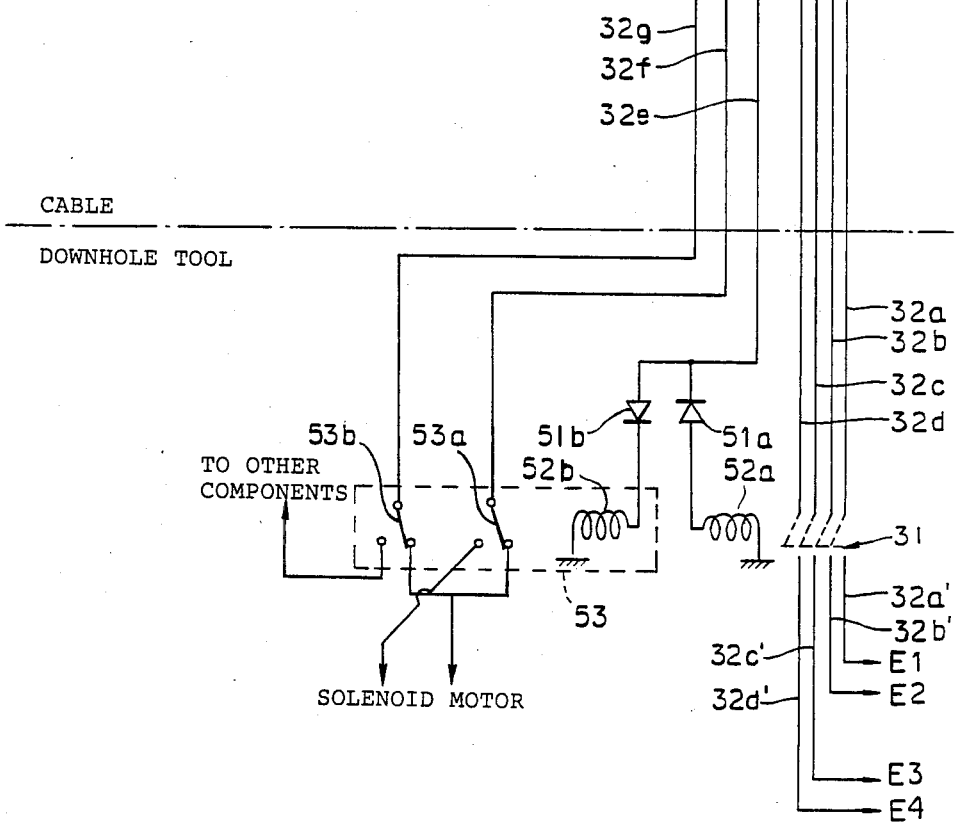
Fig. 6

METHOD, SYSTEM, AND TOOL FOR INVESTIGATING BOREHOLE CASINGS

TECHNICAL FIELD

This invention relates to systems, tools, and methods for investigating casings which are fitted into boreholes that traverse earth formations. More particularly, this invention relates to borehole casing diagnostic systems, tools, and methods which are suitable for use in evaluating and/or optimizing the cathodic protection of casings and which may be used for finding the location and rate of casing corrosion.

BACKGROUND OF THE INVENTION

When a metal pipe or casing is fitted into a borehole, the metal will be liable to corrode as the fluids present in the borehole are potentially corrosive. Because an earth formation may include several different layers, large scale electrochemical cells can be set up between the parts of the casing contacting the different layers, so that in some regions, net current enters the casing from the formation while in other regions net current leaves the casing and flows into the formation. Where net current in the form of metal ions leaves the casing, the casing will corrode gradually. It is known that the rate of such corrosion can be in the order of mm/year, which is proportional to an outgoing current on the order of microamps/cm$^2$. Since this electrochemical corrosion results from the current leaving the casing, the corrosion can be prevented if the casing is maintained at a potential such that net current enters the casing over its entire length. For this purpose, cathodic protection is often used. Cathodic protection is well known in the art, and prevents the electrochemical corrosion of a metal casing fitted in a borehole traversing an earth formation by making the metal casing into the cathode of an electrochemical cell.

In order to determine whether cathodic protection is needed for a casing, and in evaluating and/or optimizing the cathodic protection applied to a particular casing, the potential profile of the casing along its longitudinal direction is measured. The equipment for providing a typical potential profile for a casing is illustrated in FIG. 1. As shown, from ground surface 1 a borehole 2 traverses an earth formation which may include various different layers of different compositions. Fitted into the borehole 2 is a casing 3 which is typically comprised of a series of metal pipes connected in end-to-end relation. The equipment for measuring the potential profile of the casing typically comprises a downhole tool 4 which is suspended by a downhole cable 5 via a winch or pulley 6. The downhole tool 4 is provided with a pair of top and bottom electrodes 4a and 4b each of which is typically comprised of an electrically conductive roller so that the roller electrodes 4a and 4b may roll along the inner peripheral surface of the casing 3 as the downhole tool 4 moves up and down along the casing 3. Of course, the roller electrodes 4a and 4b are rotatably supported and electrically isolated from each other by a mass isolation joint 4c. The cable 5 includes at least two conductors, one for each of the roller electrodes 4a and 4b, and it is connected to a voltmeter 7. Accordingly, the potential difference between the roller electrodes 4a and 4b may be measured easily by the voltmeter 7 and the potential difference measurements may be carried out from point to point as the downhole tool is moved either upward or downward along the casing 3.

FIG. 2 illustrates a typical casing potential profile curve obtained by the equipment shown in FIG. 1. In FIG. 2, the ordinate represents the depth of the casing 3 from the ground surface 1 and the abscissa represents in microvolts the reading of the voltmeter 7. The depth of the downhole tool 4 from the ground surface 1 or top of the casing 3 is preferably determined to be the center point between the top and bottom electrodes 4a and 4b at the site of measurement. For the purpose of illustration, it is assumed that the solid line curve was obtained by running the downhole tool 4 along the casing 3 when the casing 3 was without cathodic protection. As indicated in FIG. 2, the solid line curve has four regions of interest. The section of the solid line curve indicated by I is a region having a negative voltmeter reading which is indicative of current flowing in a downward direction along the casing 3 in this region. On the other hand, the section of the curve indicated by II has a positive voltmeter reading and indicates the presence of upgoing current through the casing 3 in this region. Further, the curve includes a region III where the slope of the curve is negative, indicating the presence of current leaving the casing 3 radially, whereas, region IV of the curve has a positive slope which indicates that current enters the casing 3 in this region. As set forth previously, cathodic protection is generally needed if a region such as region III is present in the potential profile curve of a casing.

Where it is found that current is leaving the casing, some means such as seen in FIG. 3 must be provided to make the casing 3 entirely cathodic. In FIG. 3, a cathodic protection technique is used to cause the casing 3 to become a cathode with respect to the entire surroundings. Thus, a d.c. power supply 8 is provided with its negative polarity terminal connected to the casing 3 and its positive polarity terminal connected to an anode bed 9 embedded in the earth at a distance away from the casing 3. By providing the anode 9, a current flow from the anode 9 through the earth formation and into the casing 3 is produced, thereby counteracting or preventing a radially outward current flow from the casing. When the casing potential profile is measured under this cathodic condition, a curve as indicated by the dotted line in FIG. 2 is typically obtained. It should be appreciated that the microvolt value of the dotted line is always positive, thereby indicating the upward flow of current through the casing 3. Moreover, the slope of the dotted line is always positive, thereby indicating net current entering the casing 3 over its entire length. Thus, if the dotted line curve is obtained, one can be sure that the casing 3 is protected to some degree.

It is to be noted that a casing potential profile curve as shown by the dotted line in FIG. 2 is not always obtained. Often the casing potential curves show many changes in slope. These changes could either correspond to changes in the axial current resulting from current entering or leaving the casing radially, to the flow through the casing of an essentially constant axial current where the resistance of the casing is varying, or most likely to a combination of the two effects. One reason for the casing resistance to vary is the existance of electrochemical corrosion which is often concentrated locally. Thus, it is often desirable to find the location of severe corrosion and the rate of corrosion. Knowing the location and the rate, one can take various possible alternative measures which would maximize the usage of the casing 3. In order to evaluate the degree of cathodic protection or rate of corrosion, it is necessary to measure with high accuracy both the potential difference along the casing and the local casing resistance. After these parameters are measured, one can calculate the local current flowing along the casing, which, in turn, allows one to calculate the value of the radial current leaving the casing 3.

Some techniques for determining local currents along a casing have been proposed, such as are disclosed in U.S. Pat. No. 2,459,196, issued to W.H. Stewart on Jan. 18, 1949, and U.S. Pat. No. 4,431,964, issued to A. M. Walkow on Feb. 14, 1984. However, these prior art techniques are more or less insufficient in accuracy and are limited to operation in wells which contain insulating fluid such as diesel oil or gas. The requirement for having a nonconductive fluid in the casing in order to perform a corrosion evaluation is particularly limiting, because during repair, overhall, and maintenance operations when such an evaluation is often desired, wells often contain conductive fluids such as brine. The conductive fluid must then be displaced by diesel oil before the prior art techniques can be used. Thus, there has been a need for a new technique which can provide more accurate measurements and be operable in any well fluid, thereby saving time and expense involved in pretreating the well prior to investigation.

SUMMARY OF THE INVENTION

It is therefore an object of the present invention to obviate the disadvantages of the prior art as described above and to provide an improved system, tool, and method for investigating borehole casings.

It is another object of the present invention to provide a system for investigating borehole casings where the system is capable of either determining the necessity of applying cathodic protection, or evaluating and/or optimizing the cathodic protection applied to the casing in a borehole.

It is a further object of the present invention to provide a system and method for investigating borehole casings which are capable of determining the local current flowing along the casing, and the location and rate of local corrosion at high accuracy.

It is a still further object of the present invention to provide a downhole tool for use in a system for investigating a borehole casing, which is capable of being used when submerged in a relatively conductive well fluid, such as brine, without a deterioration in performance.

In accordance with the objects of the invention, a system for investigating a borehole casing generally comprises: a measurement control unit located on or about the formation surface; a downhole tool capable of investigating the casing along the length of the casing; and a cable with one end of the cable connected to the downhole tool and the other end connected to the measurement control unit, wherein the cable has a plurality of first connection lines. In accord with the system invention, the tool for investigating a borehole casing generally comprises: at least a pair of longitudinally spaced electrodes; means for causing the pair of electrodes to be contacted with the inner peripheral surface of the casing; at least a pair of second connection lines, each of which has one end connected to its corresponding electrode; and relay means interposed between the first connection lines of the cable and the second connection lines of the tool. When the relay unit is in a first position, the first connection lines of the downhole cable are short-circuited. When the relay is in a second position, the first connection lines are connected to the corresponding second connection lines thereby establishing an electrical connection between the measurement control unit of the system and the electrodes of the downhole tool.

In accord with the system and method inventions, electrical measurements of the casing are accomplished by arranging the relay in its first position such that the first connection lines of the downhole cable are short-circuited, and any drifting thermoelectric potential differences occurring in the first connection lines of the downhole cable, which are relatively long, are measured. Then, by moving the relay into its second position to establish electrical connection between the measurement control unit and the electrodes of the downhole tool, measurements of any electrical property, such as potential difference or electrical resistance across the electrodes are measured. With the provision of such a relay unit, the potential differences occurring in the first connection lines can be suitably subtracted from the potential difference measurement of the system with the relay in the second position, thereby providing a corrected potential differene determination along the casing. Moreover, in the case of resistance measurements, the large resistance of the downhole cable (which drifts with temperature) can also be suitably eliminated.

The use of such a relay unit provided in the downhole tool allows reliable data to be obtained at an increased speed because there is no wait time for the conductors of the downhole cable to reach an equilibrium condition. However, there still can be some inaccuracy or scatter in the obtained data due to, e.g. the inability of the electrodes to properly contact the casing walls because of wall corrosion. Thus, in accord with the system and method inventions, a quality control is introduced to screen the obtained data so as to determine whether the data is suitable for use. In accord with the screening process, the contact resistance of the electrodes when in contact with the inner peripheral surface of the casing (i.e. the contact resistacce being the resistance due to corrosion or poor contact with the casing wall) is also measured. The contact resistance information is then used to establish a reference value which is used as a quality control to screen the other measurements. Thus, in accord with this preferred embodiment, the potential difference measurements are treated to be valid only when the corresponding contact resistance is very small, or less than the reference value.

In accordance with a further aspect of the present invention, the downhole tool for use in evaluating a borehole casing is provided with electrodes which are substantially enclosed in an electrically insulating material except for a predetermined section of the electrode which comes into contact with the inner peripheral surface of the casing. With this structure, when the electrodes are pressed against the casing for taking measurements, the electrodes are not exposed to well fluid. Thus, even if the well fluid in which the downhole tool is submerged is a relatively electrically conductive fluid, such as brine, any leakage path between the electrodes through the conductive fluid is substantially prevented. As a result, the downhole tool can be used in any kind of well fluids, thereby eliminating the step of displacing the well fluid with diesel oil which was typically required by the prior art before potential difference measurements could be taken.

Other objects, features, and advantages of the invention will become apparent to those skilled in the art upon reference to the following detailed description of the invention and the accompanying drawings where like elements are indicated by like reference characters.

DESCRIPTION OF THE DRAWINGS

FIG. 1 is a schematic diagram of a typical system for measuring the potential profile of a borehole casing;

FIG. 2 is a hypothetical graph which might be obtained by the equipment of FIG. 1 showing potential profile curves of a borehole casing before and after cathodic protection of the casing;

FIG. 3 as a schematic diagram of a typical system for the cathodic protection of a borehole casing;

FIGS. 4a and 4b are schematic diagrams showing various aspects of the downhole tool of the invention in unanchored and anchored positions respectively within a casing;

FIG. 5b is a schematic, transverse cross section along line V—V of FIG. 5a;

FIG. 6 is a part block part schematic diagram of the system invention for investigating a borehole casing;

DETAILED DESCRIPTION OF THE PREFERRED EMBODIMENTS

Figure 5A:
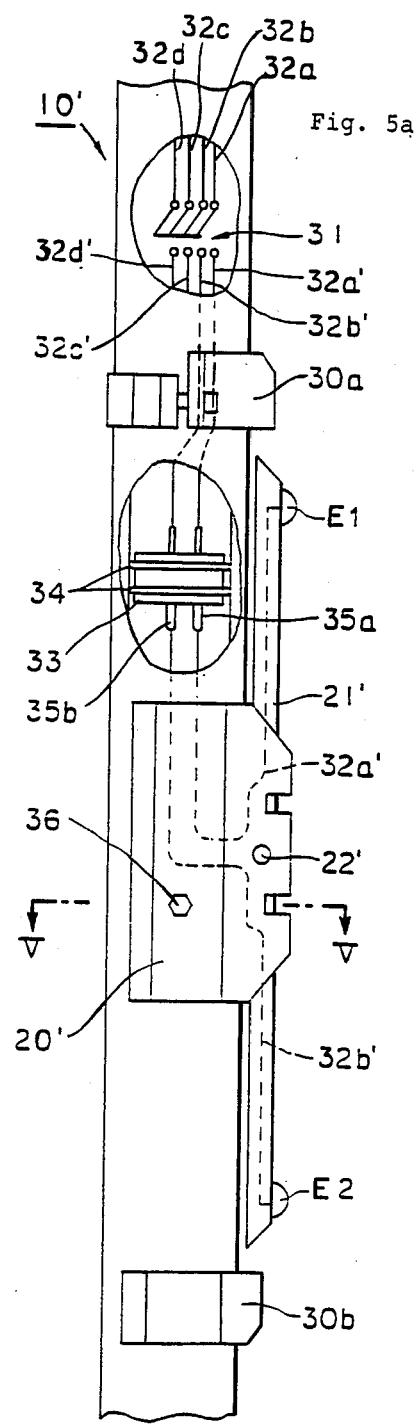
FIG. 5a is a schematic diagram of a section of a modified tool of the invention.

Turning to FIGS. 4a and 4b, a downhole tool 10 constructed in accordance with one embodiment of the system invention for investigating a borehole casing is seen. FIG. 4a shows tool 10 in a non-operative condition in which the downhole tool 10 is not pressed against the casing 3. FIG. 4b, on the other hand, shows tool 10 in an operative condition, where the tool 10 is pressed against the casing 3. The downhole tool 10 comprises a top head 12 which is mechanically coupled to a downhole cable 11 which itself is typically comprised of a plurality of connection lines. As discussed hereinafter, the downhole cable 11 extends upward along the casing 3 and is connected to a measurement control unit located at or about the formation surface. The downhole tool 10 also includes a pair of mechanical coupling adapters 13a and 13b and a pair of mass insulation adapters 14a and 14b for electrically isolating the downhole tool from the cable and the upper and lower portions of the tool from each other, respectively. Also provided in the downhole tool 10 is an electrical cartridge 15 which includes various electrical and electronics components for controlling the operation of the downhole tool 10. A hydraulic section 16 is located adjacent to the electrical cartridge 15, followed by a driver section 17. Together, the hydraulic section 16 and driver section 17 function to control the pivoting motion of a pair of arms 25a and 25b which are pivotally mounted on the driver section 17. A bottom head 18 is provided at the bottom of the downhole tool 10 with the two adapters 13b and 14b being interposed between the bottom head 18 and the driver section 17.

The downhole tool 10 is further comprised of a pair of electrode assemblies 20a and 20b. The top electrode assembly 20a is fixedly mounted on the hydraulic section 16. The electrode assembly 20a includes a support beam 21a which is pivotally supported at a pivot 22a. Support beam 21a supports two electrodes E1 and E2, one at each end of the beam 21a. Similarly, the bottom electrode assembly 20b is fixedly mounted on the bottom head 18 and includes a support beam 21b which is pivotally supported at a pivot 22b. Support beam 21b likewise supports two electrodes E3 and E4, one at each end of the beam 21b. Support beams 21a and 21b may be straight, or if desired, suitably bent as shown in FIGS. 4a and 4b. Since the support beams 21a and 21b are pivoted at their centers, with their respective electrodes E1 and E2, and E3 and E4 located at the beams' ends, all of the four electrodes E1 through E4 may be brought into contact uniformly with the inner peripheral surface of the casing 3 when pressed thereagainst even if the inner surface is not even. Those skilled in the art will appreciate that the inner surface may be uneven for many reasons including unevenness as a result of the formation of a corroded layer, removal of some metal as a result of corrosion, or as a result of a curvature of the casing. In the preferred embodiment, the so-arranged electrode array is arranged with a two foot spacing between the top two electrodes E1 and E2, a ten foot spacing between the inner electrodes E2 and E3, and a two foot spacing between the bottom two electrodes E3 and E4. It should be appreciated, however, that the spacing between any two electrodes may be arbitrarily determined.

As described previously, the arms 25a and 25b provide a means for forcing the downhole tool 10 against the casing wall and these arms are supported at pivots 28a and 28b, respectively. Although not shown, it will be understood that the arms 25a and 25b are operatively coupled to any suitable mechanism and hydraulic cylinder mounted inside of the sections 16 and 17 which can control the pivotal movement of the arms 25a and 25b. The arms 25a and 25b are also provided at their free ends with horizontal bars 26a and 26b, respectively. The combination of the arm 25a and bar 26a, or 25b and 26b, will be seen to define an L-shaped member, and a roller 27a or 27b, is provided at the outside of the elbow of each of these L-shaped members. The rollers 27a and 27b, which are preferably comprised of an electrically insulating material, are mounted on the elbows in a freely rotatable manner. Thus, as shown in FIG. 4a, when the arms 25a and 25b are arranged in their retracted positions, they extend in a position parallel with the longitudinal axis of the downhole tool 10 and with the rollers 27a and 27b not contacting the casing 3. However, when the arms 25a and 25b are pivoted clockwise, their insulator rollers 27a and 27b are brought into contact with one side of the inner peripheral surface of the casing 3 thereby causing the four electrodes E1 through E4 to be pressed against the other side inner peripheral surface of the casing 3. Because the electrodes E1 through E4 are mounted on pivoted support beams 21a and 21b, all of the electrodes E1 through E4 are uniformly brought into contact with the casing 3 as shown in FIG. 4b. This preferred arrangement, with rollers 27 and 27b, permits the downhole tool 10 to be moved vertically along the casing 3 even when the tool is in its engaged (actuated) position, as the electrodes E1 through E4 may slide on the inner surface of the casing 3. Such a feature is advantageous in taking local fine measurements by traversing the downhole tool 10 longitudinally over a limited amount of distance without releasing the actuated condition shown in FIG. 4b.

Although not shown specifically in FIGS. 4a and 4b, it should be understood that a relay unit is provided as part of the downhole tool 10, and is preferably located as close to the electrodes as possible in order to minimize the number of connections between the relay and the electrodes. The relay unit functions to controllably connect or disconnect the internal connection lines of the downhole tool 10 (which lead to the electrodes E1 through E4) to the connection lines of the downhole cable 11. As will be discussed hereinafter, such a relay unit has two positions. In a first position, the relay disconnects the internal connection lines of the downhole tool 10 from the downhole cable 11 and shorts the connection lines of the downhole cable 11 together. In a second position, the connection lines of the downhole cable 11 are electrically connected to the internal connection lines of the downhole tool 10.

Figure 5B:
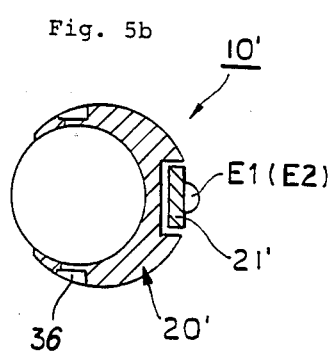

FIGS. 5a and 5b show part of another downhole tool 10' which is slightly modified from, but is basically the same in structure with the downhole tool 10 shown in FIGS. 4a and 4b. As shown in FIG. 5a, the downhole tool 10' is provided with a relay unit 31 which is connected at one end to four connection lines 32a through 32d of the downhole cable 11 and at the opposite end to four corresponding internal connection lines 32a' through 32d' of the downhole tool 10'. As described above, the relay unit 31 can take two positions. In a first position, as indicated in FIG. 5a, all of the four connection lines 32a through 32d are electrically connected together thereby establishing a short-circuited condition. On the other hand, in its second position, each of the four connection lines 32a through 32d is electrically connected to the corresponding one of the four internal connection lines 32a' through 32d" via relay unit 31. Although not shown specifically in FIG. 5a, it will be seen hereinafter that the relay unit 31 includes an electromagnet and the position of the relay unit 31 is electromagnetically controlled.

Among the four internal connection lines, two of the lines 32a' and 32b' extend through a bulkhead 33 via respective connectors 35a and 35b and through the support beam 21' to respective electrodes E1 and E2 which are located at opposite ends of the beam 21'. The bulkhead 33 is fixed in position with a pair of O-rings 34 fitted between the bulkhead 33 and the housing of the downhole tool 10' for sealing the space in which the relay unit 31 is provided. It is to be noted that the connection lines 32 are all preferably comprised of an electrical conductor coated with an insulating material. It should also be noted that the connection lines 32c' and 32d' extend along the downhole tool 10' and are connected to the remaining electrodes E3 and E4.

The downhole tool 10' of FIG. 5a is provided with an electrode assembly 20' which is fixedly attached to the housing of the downhole tool 10' by means of bolts 36. The electrode assembly 20' also includes the support beam 21' which extends substantially in parallel with the longitudinal axis of the downhole tool 10' and which is pivoted at a pivot 22'. The support beam 21' may therefore pivot around the pivot 22' and allow the two electrodes E1 and E2 to be brought into contact with the casing 3 in a uniform manner when pressed thereagainst The downhole tool 10' is also provided with a pair of protectors 30a and 30b which are securely attached to the housing of the downhole tool 10' at the top and bottom of the electrode assembly 20'. These protectors 30a and 30b are provided to protect the electrode assembly 20' by preventing the electrode assembly 20' from coming into engagement with any undesired object, such as the top of the casing 3 or liner when the downhole tool 10' is lowered into the casing 3 or liner.

Turning to FIG. 6, the overall system for investigating a borehole casing which traverses an earth formation is shown in accordance with one embodiment of the present invention in which the downhole tool described above may be advantageously used. As shown, the system for investigating a borehole casing basically comprises three sections: a measurement control unit at or around ground level; a downhole tool capable of investigating the casing along the length of the casing; and a downhole cable extending between the measurement control unit and the downhole tool, the cable including a plurality of connection lines. In the illustrated embodiment, the measurement control unit at ground surface includes a contact box 40 which defines, in effect, an interface between the measurement control unit and the downhole cable. The contact box 40 is connected to a power supply 41 which supplies electrical power in the form of voltage and current, as required. The contact box 40 is also connected to a scanner 42 which scans the measurement signals received from the plurality of electrodes mounted on the downhole tool. The scanner 42 is connected to a digital voltmeter or DVM 43, which functions not only as a voltmeter to provide voltage readings, but also as an ohmmeter to provide selective resistance readings. When the DVM 43 is selected to function as an ohmmeter, it injects a known current in the circuit from which an electrical resistance is to be measured. Both the scanner 42 and the DVM 43 are connected to a computer 44, e.g., a PC 9801 manufactured by the Nippon Electronics Corporation, a HP85 manufatured by the Hewlett-Packard Corporation, or a PDP11 manufactured by the Digital Equipment Corporation. The computer 44 in turn, is connected to a printer 45 which serves as an output device, and preferably also to a keyboard 46 which serves as a man-machine interface.

In the illustrated embodiment, the cable extending between the measurement control unit at ground surface and the downhole tool at a depth inside of the casing includes seven connection lines 32a through 32g, each of which is comprised of an insulator-clad conductor. Four connection lines 32a through 32d are connected to the contact box 40 at points A, B, C and D, respectively, and are used for communication lines with the respective four electrodes E1 through E4 of the downhole tool. Thus, the connection lines 32a through 32d extend partly into the downhole tool and are connected to the internal connection lines 32a' through 32d' via the relay unit 31. The relay unit 31 includes an electromagnet 52a which has one end connected to ground and its other end connected to the connection line 32e of downhole cable via a diode 51a. The connection line 32e is also connected via a diode 51b to one end of another electromagnet 52b, which has its other end connected to ground. The diode 51b is arranged in opposition to the diode 51a. The downhole tool also includes another relay 53 which is comprised of a pair of switches 53a and 53b which are associated with the electromagnet 52b. Switches 53a and 53b cause the connection lines 32f and 32g to be connected to a driving motor (not shown) mounted inside of the downhole tool when the switches are arranged as indicated in FIG. 6. In such a state, and when the electromagnet 52b is energized, driving energy is supplied to the motor. The motor causes the arms 25a and 25b of the downhole tool to be pivoted, thereby closing the arms and disconnecting the downhole tool from the casing 3. On the other hand, when the relay 53 is off, the switch 53a causes the connection line 32f to be connected to a solenoid (not shown). The solenoid is provided in the downhole tool for deactivating the hydraulic cylinder, thereby causing the arms 25a and 25b to open under the force of the springs 29a and 29b. At the same time, the switch 53b causes the connection line 32g to be disconnected from the motor and connected to other components, such as a gamma ray device and a casing collar locator, which are mounted inside of the downhole tool. Those skilled in the art will appreciate that the gamma ray device and/or casing collar locator may be used to determine the depth of the downhole tool along the casing 3.

Figure 7A:
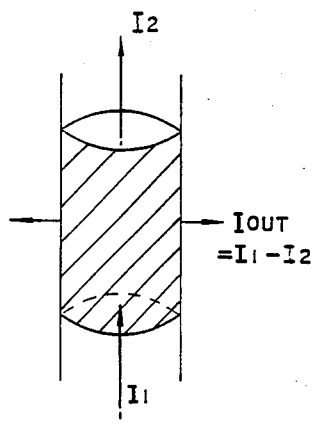
FIGS. 7a and 7b are schematic diagrams useful for explaining the principles of the measurement scheme of the invention.
Figure 7B:
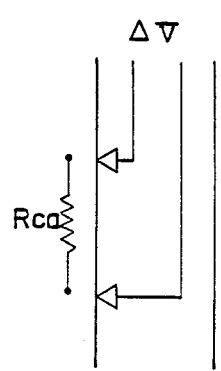

As aforestated, an object of the present invention is a highly accurate determination of the rate of local corrosion at a point along the longitudinal axis of the casing 3. In order to make such determination, the radial outward current $I_{OUT}$ leaving the casing, as indicated in FIG. 7a, must be determined. Since this radial outward current $I_{OUT}$ is the difference between the local currents $I_1$ and $I_2$ at any two points along the longitudinal axis of the casing 3, it is preferable that the local current I flowing along the longitudinal axis of the casing 3 be determined as precisely as possible. Since this local current I flowing along the casing 3 cannot be measured directly, it must be determined according to the Ohm's law from the local potential difference delta V ($\Delta V$) and the casing resistance $R_{ca}$ present across any two points along the longitudinal axis of the casing 3, as shown in FIG. 7b. It should thus be understood that the closer one makes the distance between the two electrodes for measuring the potential difference $\Delta V$ and casing resistance $R_{ca}$ therebetween, the more precisely one may determine the local current I along the casing 3, and the higher becomes the longitudinal resolution. However, in general, the closer the distance between the electrodes, the lower the potential difference and casing resistance which are to be measured. Thus, the potential differences and casing resistances must be measured as accurately as possible.

With the foregoing in mind, the operation of the system shown in FIG. 6 will now be described. After locating the downhole tool 10 at the desired depth in the casing, and after pushing the electrodes into contact against the casing 3, stationary measurements are made preferably in three steps. First, potential difference ($\Delta V$) measurements are taken. Then, contact resistance ($R_{co}$) measurements are taken. Finally, casing resistance ($R_{ca}$) measurements are preferably taken. This stationary measurement cycle may be triggered manually by the operator via the keyboard 46, or if desired, in an automatic manner at predetermined depths or depth intervals. As described previously, and in accordance with the present invention which includes the relay unit 31 as part of the downhole tool 10, the potential difference ($\Delta V$) and contact resistance ($R_{co}$) measurements are each carried out in two substeps, i.e., first with "relay on" and then with "relay off". In this manner, the effect of thermal EMFs and cable resistance on the potential difference and contact resistance measurements may be eliminated. In the illustrated embodiment, since there are four electrodes E1 through E4, there are six possible electrode pair combinations. Thus, in the preferred embodiment, the potential difference and contact resistance measurements are carried out for all of six combinations.

Accordingly, the measurement scheme for measuring the potential difference $\Delta V$ and contact resistance $R_{co}$ includes the following substeps:

Relay 31 ON: $\Delta V$ measured between A-B, B-C, C-D, A-D, A-C and B-C

Relay 31 OFF: $\Delta V$ measured between A-B, B-C, C-D, A-D, A-C and B-C

Relay 31 ON: $R_{co}$ measured between A-B, B-C, C-D, A-D, A-C and B-C

Relay 31 OFF: $R_{co}$ measured between A-B, B-C, C-D, A-D, A-C and B-C

In addition, the measurement scheme also preferably includes a step for measuring the casing resistance $R_{ca}$ which is carried out by passing a known current $I_{app}$ (e.g. 0.5 amps) between the two outer electrodes E1 and E4 and measuring the change in potential difference for the two inner electrodes E3 and E3, as follows:

Relay 31 OFF: $\Delta V$ measured between E2 and E3 with $I_{app}$ d.c. current across E1 and E4.

In particular, when making the casing resistance measurement, in order to overcome the problems of noise pickup or cross-talk, it is preferable to make a number of successive readings and average them.

With the foregoing data thus collected, the measurement control unit can determine the true potential difference $(\Delta V)_{true}$ and contact resistance $(R_{co})_{true}$ and the casing resistance $R_{ca}$ according to the following formulas:

$$(\Delta V{:}Ei\text{-}Ej)_{true} = (\Delta V{:}Ei\text{-}Ej)_{OFF} - (\Delta V{:}Ei\text{-}Ej)_{ON} \quad (1)$$
$$(R_{co})_{true} = (R_{co})_{OFF} - (R_{co})_{ON} \quad (2)$$

$$R_{ca} = \frac{((\Delta V{:}E2\text{-}E3)_{with} - (\Delta V{:}E2\text{-}E3)_{without})}{I_{app}} \quad (3)$$

In equations (1)–(3), the combination of i and j indicates any combination of two electrodes of the electrodes numbered one through four; subscripts "ON" and "OFF" indicate that the relay 31 is on and off, respectively; and subscripts "with" and "without" indicate that the known current of $I_{app}$ is present and absent, respectively.

In this manner, with the relay 31 turned on and off during the potential difference and contact resistance measurements, the true values of both the potential difference and contact resistance can be obtained without being adversely affected by the long conductors of the downhole cable. Nonetheless, some offset or inaccuracy in the data thus collected may still be present from various uncontrollable reasons. Thus, in accordance with the preferred mode of operation, the data is screened based on the derived contact resistance values. Data for which the contact resistance data are found to be equal to or smaller than a derived reference value, are designated as valid data for use in data processing. This aspect will be described with particular reference to FIGS. 8 and 9 hereinbelow.

Figure 8:
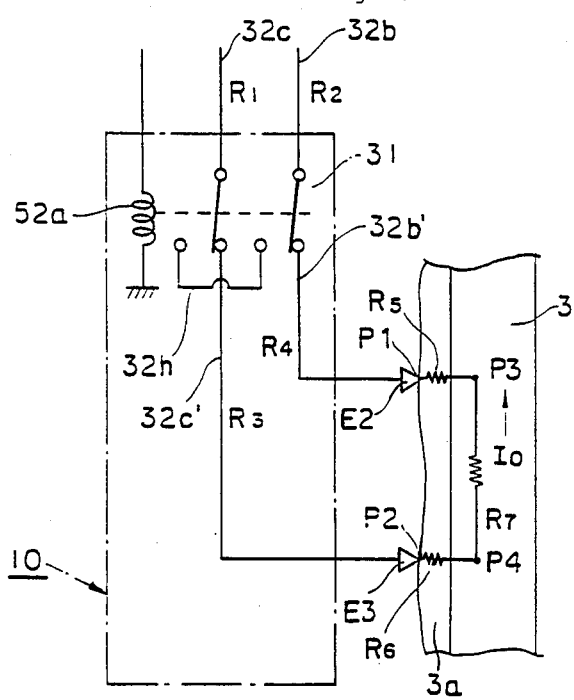
FIG. 8 is a schematic diagram which is useful for explaining the quality control scheme of the invention.

As seen in FIG. 8, a corroded layer 3a, which can be an oxide or salt of the metal casing 3 or scale, is formed at the inner peripheral surface of the casing 3. For the sake of brevity, only two electrodes E2 and E3 are shown in FIG. 8 with regard to the downhole tool, but all the electrodes are assumed to be formed in the shape of a knife-edge as shown so as to allow them to cut effectively through the corroded layer 3a and to come into contact with the casing 3 proper. However, even with such a knife-edge structure, proper contact between the electrodes and the casing 3 proper cannot be ensured. Indeed, if the corroded layer 3a formed on the casing 3 is relatively thick and highly resistive, then the electrodes E1 through E4 may not be able to cut through the corroded layer 3a, as indicated in FIG. 8, even though they are formed in the shape of a knife-edge. In this case, appreciable contact resistances, which are indicated by R5 and R6 in FIG. 8, respectively exist between the electrodes E2 and E3 and the casing 3. If such contact resistances (R5 and R6) are present, the potential difference measured across the two electrodes E2 and E3 at points P1 and P2 on the surface of the corroded layer 3a will differ from the potential difference present across the corresponding two points P3 and P4 in the casing 3. However, as previously indicated, a measurement of the potential difference across any two points spaced apart along the longitudinal axis of the casing 3 itself (e.g. P3 and P4) is what is desired. Thus, a scheme to check that the electrodes E1 through E4 are all, in fact, in proper electrical contact with the casing 3 itself is advantageously suggested. If the contact resistances R5 and R6, alone or together are significant at certain locations along the casing, then the potential difference data measured across the electrodes E2 and E3 at those locations are invalid and are preferably discarded.

It can be shown that there is an upper limit for the contact resistance beyond which a significant potential difference exists across the corroded layer. This limit depends on the kind of fluid inside the casing 3. In the case where the fluid inside of the casing 3 is relatively insulating, such as air, diesel oil or the like, the upper limit is a few tens of ohms. When the casing 3 is filled with a fluid which is conductive or polar, such as water, brine or the like, the upper limit for the contact resistance is only a few hundredths of an ohm. Thus, if the contact resistance is lower than this upper limit, the potential drop across the contact resistance can be considered to be negligible, and the potential difference measured across the electrodes E2 and E3 is substantially equal to the potential difference existing across the casing resistance R7 between the two points P3 and P4. Such being the case, it is important to measure the contact resistance for each of the electrodes E1 through E4 as a quality control.

It will now be described how this quality control can be carried out in the system of FIG. 6 starting from the further analysis based on the structure shown in FIG. 8. As pointed out previously, FIG. 8 is a highly schematic diagram showing only selected elements of the downhole tool 10 which is pressed against the corroded layer 3a of the casing 3. The nomenclature in FIG. 8 is defined as follows:

$R_1$: Resistance of cable connection line 32c
$R_2$: Resistance of cable connection line 32b
$R_3$: Resistance of wire 32c and electrode E3
$R_4$: Resistance of wire 32b' and electrode E2
$R_5$: Contact resistance of electrode E2
$R_6$: Contact resistance of electrode E3
$R_7$: Casing resistance of casing 3
$I_O$: Casing current When making resistance measurements from the ground surface using the DVM 43 as an ohmmeter, electromagnet 52a is energized, thus turning relay 31 "on" and simultaneously short-circuiting the cable connection lines 32b and 32c. The resistance $R_{ON}$ measured through the short-circuited path 32h gives $$R_{ON}=R_1+R_2 \tag{4}$$

Then, the relay 31 is turned off with the deenergization of electromagnet 52a, thereby causing the cable connection lines 32b and 32c to be electrically connected to the internal connection lines 32b' and 32c, respectively. The resistance $R_{OFF}$ measured under this condition gives $$R_{OFF}=R_1+R_2+R_3+R_4+R_5+R_6+R_7 \tag{5}$$

Thus, the differential resistance between the ON and OFF conditions can be determined as follows:

$$R_{OFF}-R_{ON}=R_3+R_4+R_5+R_6 \tag{6}$$

It is to be noted that the last term $R_7$ is omitted in equation (6) because it is in the order of approximately $10^{-5}$ ohms and thus negligible in comparison to the rest.

The obtained $R_{OFF}-R_{ON}$ must then be corrected for the potential difference in the casing 3. As pointed out previously, in making a resistance measurement using the DVM 43 as an ohmmeter, the DVM 43 injects a known current $i_m$ (e.g. 1.0 mA) into the circuit to be measured, and thus, the current $i_m$ passes through the closed circuit including resistances R1 through R7. However, in the present case, a potential difference already exists in the casing 3 due to the corrosion current $I_O$ flowing in the casing 3 along its longitudinal direction. This potential difference is included in the potential difference measurement taken between the electrodes E2 and E3. Accordingly, the potential difference $V_m$ measured by the DVM 43 during the contact resistance measurement step may be expressed as $$V_m=i_m R_{OFF}+I_O R_7 \tag{7}$$

Thus, the resistance $R_m$ measured by the DVM 43 is $$R_m=V_m/i_m=R_{OFF}+I_O R_7/i_m \tag{8}$$

This indicates the fact that the resistance measured by the DVM 43 functioning as an ohmmeter includes a resistance defined by $I_O R_7/I_m$ resulting from the corrosion current $I_O$ flowing along the casing 3 at the site of measurement, as indicated by the last term in the above equation. Thus, the apparent differential resistance $(R_{OFF}-R_{ON})_{apparent}$ which is obtained by taking a difference between the two resistance readings by the DVM 43 with the relay 31 on and off may be expressed by the following equation.

$$(R_{OFF}-R_{ON})_{apparent}=(R_3+R_4+R_5+R_6)+I_O R_7/i_m \tag{9}$$

Consequently, in order to obtain a true differential resistance $(R_{OFF}-R_{ON})_{true}$ which is equal to the sum of $R_3+R_4+R_5+R_6$, the corrosion current term $I_O R_7/i_m$ must be subtacted from the difference between the measured $R_{OFF}$ and $R_{ON}$. This can be expressed as follows:

$$(R_{OFF}-R_{ON})_{true}=R_3+R_4+R_5+R_6=(R_{OFF}-R_{ON})_{measured}-I_O R_7/i_m \tag{10}$$

where, $I_O R_7 = (\Delta V : E2-E3)_{true}$.

Figure 9:
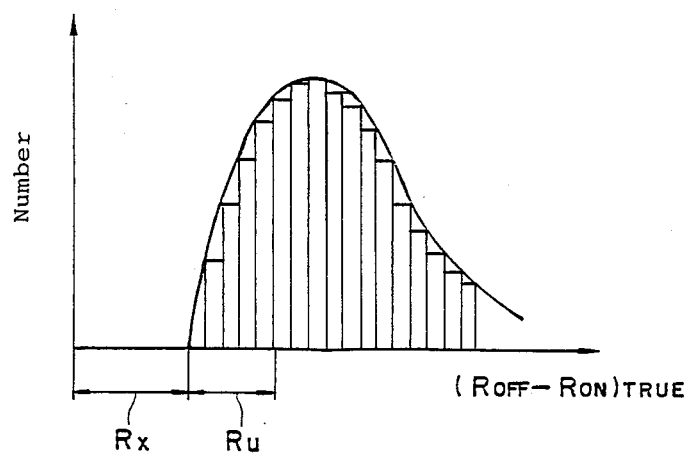
FIG. 9 is a histogram graph which is useful for explaining the quality control scheme of the invention.

With the value $(R_{OFF}-R_{ON})_{true}$ being obtained over the length of the casing, the value $(R_{OFF}-R_{ON})_{true}$ may be histogrammed as shown in FIG. 9, using a predetermined interval. If the contact resistances $R_5$ and $R_6$ are vitually zero, i.e., perfect contact conditions, we have $(R_{OFF}-R_{ON})=R_3+R_4$, ($R_7$ being negligible), which indicates that the wires 32b' and 32c are in contact through the electrodes E2 and E3 (and the casing). This value can be read off as $R_x$ from the histogram of FIG. 9. Thus, any value larger than $R_x$ indicates the presence of a finite contact resistance $R_{co}$ in the contact resistance measurement. This contact resistance is, in fact, the sum of the contact resistances for the electrode pair under consideration. Thus, based on any standard, (e.g., the nature of the well fluid in the casing 3, and/or prior experience or experiment, and/or a statistical approach), an upper limit contact resistance $R_u$, which is a sum of $R_5$ and $R_6$, may be chosen. Alternatively, the upper limit may be preset arbitrarily. With the upper limit contact resistance $R_u$ set, the potential difference measurements yielding $(R_{OFF}-R_{ON})_{true} > R_x + R_u$ are considered bad data and are rejected. In this manner, and in accordance with the preferred embodiment of the present invention, the potential difference data once collected is screened using the upper limit contact resistance thus determined as a reference so that only valid data is used in data processing for determining desired data It is to be noted that the above-described quality control scheme can be implementd by a software program stored in the computer 44 for screening the data collected for each electrode pair at each longitudinal location of the downhole tool 10 along the casing 3.

An alternative to the histogramming technique for obtaining an $R_x$ is to select the minimum $(R_{OFF}-R_{ON})$-true for each electrode pair from the collected data set and to take this value as the $R_x$. However, care must be taken not to use a spurious data point when choosing the $R_x$. It is noted that a choice of $R_u$ can be made as described above.

Figure 10A:
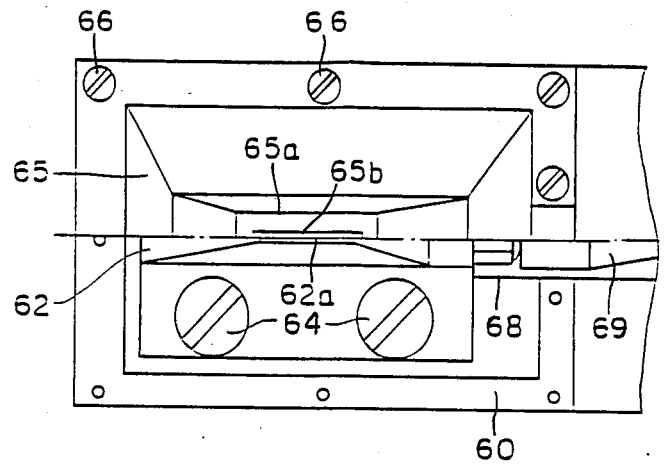
FIGS. 10a through 10c are schematic diagrams showing an enclosed electrode of the tool of the invention in accordance with one embodiment of the invention.
Figure 10B:
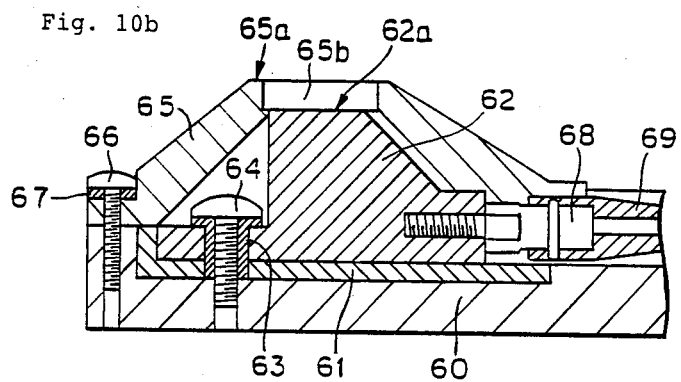
Figure 10C:
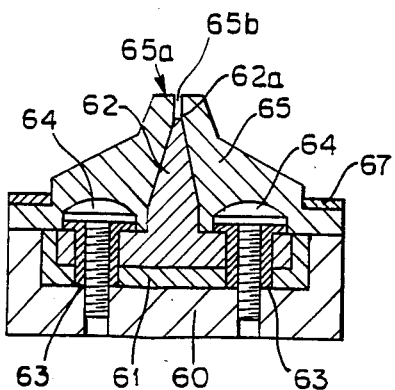
Figure 11:
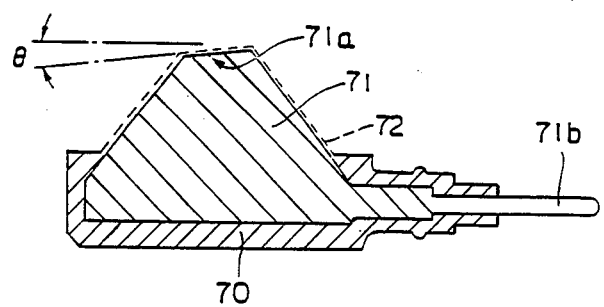
FIG. 11 is a schematic diagram showing another embodiment of the enclosed electrode structure of the tool of the invention.

Another aspect of the present invention relates to the structure of the electrodes mounted on the downhole tool and is seen with reference to FIGS. 10 and 11. As will be described in detail hereinafter, the electrodes used in accordance with the present invention are preferably single piece, enclosed structures comprised of a single metal which is of a similar metal composition to the casing 3. These features will manifest themselves as this aspect of the present invention is described with reference to FIGS. 10 and 11.

FIGS. 10a through 10c illustrate part of electrode assembly constructed in accordance with one embodiment of the present invention. As shown, this electrode assembly includes a support beam 60 on which an electrode 62 having a defined shape is mounted with an insulator pad 61 comprised of an electrically insulating material, such as ceramic, PEEK (poly-ether-ether-ketone) or epoxy. The electrode 62 is generally in the shape of an ax having a flat surface 62a elongated in shape at the apex and it is fixed in position by means of a plurality of screws 64 which are screened into the corresponding threaded holes provided in the support 60. An insulator tube 63 is fitted into each of the screws 64 thereby allowing the electrode 62 to remain insulated from the support beam 60. A rubber packer 65 is provided to cover the electrode 62 substantially excepting that portion of the electrode 62 which is exposed through a top opening 65b which is defined in a top flat surface 65a of the rubber packer 65. Therefore, the electrode 62 is substantially enclosed by an electrically insulating material and it is exposed only through the opening 65b. However, since the opening 65b is so defined that the electrode 62 is completely shielded when the electrode 62 is pressed against the casing 3 so as to be in contact therewith through the opening 65b, the electrode 62 is prevented from being exposed to the well fluid. As a result, no leakage path (for the fluid or for current) is defined.

A holding plate 67 is placed around the periphery of the base portion of the rubber packer 65. The holding plate 67 is generally rectangular in shape, and is arranged such that a plurality of screws 66 to be screwed into the corresponding threaded holes formed in the support 60 extend through it. A socket contact 68 screwed into the electrode 62 is also provided. The socket contact 68 is coated with an insulator and is enclosed in a rubber boot 69 and it extends horizontally in parallel with the support 60. It is thus clear that a shielded structure is provided in which the electrode 62 can be completely shielded from the well fluid when taking measurements by contacting the electrode 62 with the casing 3.

In the structure described above, the rubber packer 65 is provided separately and is fixedly attached to the support beam 60 to cover the electrode 62. As an alternative, molded insulating elements 61 and 65 may be provided. Furthermore, in the structure described above, the apex of the electrode 62 is recessed as compared with the apex of the rubber packer 65. However, if desired, the apex of the electrode 62 may be raised up to being level with the apex of the rubber packer 65. It is preferable that the apex of the electrode 62 does not protrude beyond the rubber packer 65 because this will allow the electrode 62 to come into contact with the well fluid when the electrode is contacting the casing.

It should further be noted that the electrode 62 is constructed as a single piece element and the socket contact 68 is directly screwed into the electrode 62. This single piece feature is advantageous as it eliminates any contact potential within the electrode 62 itself. It is also preferable that the electrode 62 be comprised of a material which is similar or identical to that of the casing 3 to prevent formation of a galvanic cell between the casing and the electrode if any conductive fluid contacts the electrode. In this respect, since the casing 3 is typically comprised of low alloy steel, this fact should be taken into account in selecting a material for the electrode 62. In addition, it is also preferable to make the electrode 62 from a single metal because this also eliminates the possibility of setting up galvanic cells within the electrode 62 should any conductive fluid come into contact with the electrode. Another important function of the insulation of the electrodes from the well fluid is to prevent passage of current through conductive fluid during the contact and casing resistance measurement steps. If appreciable current were to flow through any conductive fluid, erroneous resistance measurements might result.

Another embodiment of the electrode structure is illustrated in FIG. 11. In this embodiment, the electrode 71 is also generally in the shape of an ax, but, it has an apex 71a which is slanted at an angle $\theta$. The ax-shaped electrode 71 has its bottom half embedded in an insulator moding 70 comprised, for example, of epoxy, and its top half coated with an insulating film 72 comprised, for example, of epoxy, ceramic (e.g., alumina), Teflon (a trademark of the DuPont Corporation, Viton (a fluoroelastomer and trademark of the DuPont Corporation) or PEEK. For the rubber packer and molding, Viton is preferred, and for coating, ceramic or Teflon is preferred. Such a coating 72 may be provided all around the electrode 71, if desired. The coating 72 at the apex 71a may be removed before use, or if desired, the coating 72 can be removed appropriately when the electrode 71 is pressed against the casing 3 for the first time so that it may not be necessary to be removed manually before use. The electrode 71 is also arranged with an elongated contact 71b which is integrally formed. However, if desired, the contact 71b may be formed separately and fixedly attached to the main body of the electrode 71 such as by screwing it thereinto, for example.

As described in detail above, in accordance with the system, tool, and method inventions set forth, the potential difference and casing resistance measurements can be carried out accurately, speedily, and at high resolution. The provided systems, tools, and methods allow for a proper determination of whether the application of cathodic protection is needed for a particular casing, and provide an accurate indication of the local corrosion rate. Moreover, the provided systems, tools, and methods allow for a proper evaluation and optimization of the cathodic protection which is applied to a particular casing. Furthermore, with the application of the provided quality control scheme, the data to be used for data processing may be further refined, thereby increasing the reliability of the results obtained. In addition, with the use of an enclosed electrode structure, measurements may be carried out in any well fluid, conductive or insulating.

There has been described and illustrated herein systems, tools, and methods for investigating borehole casings. It will be appreciated that the methods disclosed herein are closely connected with the provided systems and tools. While particular embodiments of the invention have been described, it is not intended that the invention be limited thereby, as it is intended that the invention be broad in scope and the specifications be read likewise. Thus, for example, although an insulated electrode structure has been described as applied to an electrode of the stationary type only, it would be obvious for one skilled in the art to apply the insulated electrode teachings to an electrode of the rotating type using a roller. Likewise, while arms for pushing the tool against the casing have been described, other means, such as spring, for pushing the tool aginst the casing so as to bring the electrodes of the tool into contact with the casing will be readily suggested to one skilled in the art. Therefore, it will be apparent to those skilled in the art that other changes and modifications may be made to the invention as described in the specification without departing from the spirit and scope of the invention as so claimed.

I claim:

1. A system which investigates a casing fitted into a borehole traversing an earth formation, comprising:
   (a) a downhole tool capable of investigating said casing along the length of said casing;
   (b) a measurement control unit located in proximity to the surface of said earth formation; and
   (c) a cable having one end connected to said downhole tool and the other end connected to said measurement control unit, said cable including at least a plurality of first connection lines, said downhole tool comprising,
   (1) at least a first pair of longitudinally spaced electrodes,
   (2) means for causing said pair of electrodes to be contacted with the inner peripheral surface of said casing,
   (3) at least a pair of second connection lines, each of said second connection lines having one end connected to a corresponding one of said electrodes, and
   (4) relay means interposed between said first connection lines of said cable and the second connection lines of said downhole tool, said relay means being arranged to be positioned in first and second positions, wherein when said relay means is in said first position, said first connection lines of the cable are short-circuited by said relay means, and when said relay means is in said second position, said first connection lines are connected to their corresponding second connection lines thereby establishing an electrical connection between said measurement control unit and said electrodes, and
   wherein said measurement control unit includes at least means for measuring at least one predetermined electrical property with said electrodes of said downhole tool in contact with said casing, at least once with said relay means in said first position and at least once with said relay means in said second position, and means for subtracting a value obtained with said relay means in said first position from a value obtained with said relay means in said second position to provide a true value of said predetermined electrical property.

2. A system according to claim 1, wherein:
said predetermined electrical property is a potential difference present between said at least first pair of electrodes.

3. A system according to claim 1, wherein:
said predetermined electrical property is an impedance.

4. A system according to claim 3, wherein:
said impedance is an electrical resistance.

5. A system according to claim 1, wherein:
said downhole tool includes at least a second pair of longitudinally spaced electrodes, and
said measurement control unit includes current supplying means for supplying a known current between said second pair of electrodes in contact with said casing.

6. A system according to claim 5, wherein:
said downhole tool further includes a housing, and
one of said first pair of electrodes and one of said second pair of electrodes are mounted on a support beam with each electrode located on a respective end of said support beam, and said support beam is pivotally mounted on said housing of said downhole tool.

7. A system according to claim 1, wherein:
said downhole tool further includes a housing, and
said means for causing said pair of electrodes to be contacted with the inner peripheral surface of said casing includes at least an arm pivotally supported by said housing of said downhole tool and capable of being pivotally retracted and extended, whereby when said arm is retracted, said downhole tool may freely move along the longitudinal direction of said casing, and when said arm is pivotally extended, said arm is brought into pressure contact with said casing and said electrodes are brought into pressure contact with said casing.

8. A system according to claim 7, wherein:
said arm is provided with a roller which is brought into contact with said casing when said arm is pivotally extended such that said downhole tool may move along said casing with said electrodes keeping sliding contact with said casing.

9. A system according to claim 8, wherein:
said arm is further provided with a horizontal bar which extends in a direction generally perpendicular to the longitudinal direction of said downhole tool when said arm is located in said retracted position such that said electrodes are prevented from coming into contact with said casing.

10. A system according to claim 1, wherein:
said measurement control unit includes current supplying means for supplying a known current between at least said first pair of electrodes in contact with said casing,
said predetermined electrical property is a potential difference present between said at least first pair of electrodes, and
said mesurement control unit includes means for determining the contact resistance between said at least first pair of electrodes and said casing.

11. A system according to claim 10, wherein:
said means for determining the contact resistance between at least said first pair of electrodes and said casing includes means for dividing a voltage value determined in the absence of said supplied known current of the differnnce of the potential difference between said first pnair of electrodes with said relay in said second and first positions by a value for said known supplied current so as to arrive at a first resistance value, and means for subtracting said first resistance value from a second resistance value, said second resistance value being determined by supplying a known current and by taking the difference of the potential difference between said first pair of electrodes with said relay in said second and first positions while said known current is supplied.

12. A system according to claim 11, wherein:
said measurement control unit further include means for setting a threshold contact resistance, wherein said predetermined electrical property determinations are deemed valid for a given position along said casing only if a contact resistance determination made by said contact resistance determining means is below said threshold contact resistance.

13. A system according to claim 11, wherein:
said downhole tool includes at least a second pair of longitudinally spaced electrodes,
said predetermined electrical property determination includes a casing resistance determination, and
said measurement control unit includes current supplying means for supplying a second known current between said second pair of electrodes in contact with said casing and means for determining the casing resistance of said casing by dividing the value of said second known current supplied between said second pair of electrodes into the difference of the potential differences between said first pair of electrodes when said second current is applied and before said current is applied.

14. A system according to claim 13, wherein:
said measurement control unit further includes means for setting a threshold contact resistance, wherein said predetermined electrical property determinations are deemed valid for a given position along said casing only if a contact resistance determination made by said contact resistance determining means is below said threshold contact resistance.

15. A downhole tool used in a system which investigates a casing fitted into a borehole traversing an earth formation, said downhole tool being movable along the length of said casing as suspended by a downhole cable which includes at least a plurality of first connection lines, said downhole tool comprising:
at least a first pair of longitudinally spaced electrodes arranged to be capable of at least partially being brought into contact with the inner peripheral surface of said casing;
at least a pair of second connection lines, each of said second connection lines having one end connected to a corresponding one of said electrodes, and the other end connectable to a corresponding one of said first connection lines,
wherein each of said electrodes is substantially enclosed in an electrically insulating material with the portion of said electrodes which comes into contact with said casing when said electrodes are brought into partial contact with said casing being free from said insulating material, such that with a conductive fluid being inside of said casing, said electrodes are electrically insulated from each other.

16. A downhole tool according to claim 15, wherein:
said electrically insulating material for substantially enclosing said electrode is a rubber packer provided with an opening such that said portion of said electrode comes into contact with said casing through said opening.

17. A downhole tool according to claim 15, wherein:
said electrically insulating material for substantially enclosing said electrode is a rubber mold provided with an opening such that said portion of said electrode comes into contact with said casing through said opening.

18. A downhole tool according to claim 15, wherein:
said electrically insulating material for substantially enclosing said electrode is a coating deposited on each of said electrodes.

19. A downhole tool according to claim 16, further comprising:
relay means interposed between said first connection lines of said cable and the second connection lines of said downhole tool, said relay means being arranged to be positioned in first and second positions, wherein when said relay means is in said first position, said first connection lines of said cable are short-circuited by said relay means, and when said relay means is in said second position, said first connection lines are connected to their corresponding second connection lines thereby establishing an electrical connection between said electrodes and said cable.

20. A downhole tool according to claim 17, further comprising:
relay means interposed between said first connection lines of said cable and said second connection lines of said downhole tool, said relay means being arranged to be positioned in first and second positions, wherein when said relay means is in said first position, said first connection lines of the cable are short-circuited by said relay means, and when said relay means is in said second position, said first connection lines are connected to their corresponding second connection lines thereby establishing an electrical connection between said electrodes and said cable.

21. A downhole tool according to claim 18, further comprising:
relay means interposed between said first connection lines of said cable and the second connection lines of said downhole tool, said relay means being arranged to be positioned in first and second positions, wherein when said relay means is in said first position, said first connection lines of the cable are short-circuited by said relay means, and when said relay means is in said second position, said first connection lines are connected to their corresponding second connection lines thereby establishing an electrical connection between said electrodes and said cable.

22. A method of investigating a casing fitted into a borehole traversing an earth formation with a system having a downhole tool capable of investigating the length of said casing with a plurality of longitudinally spaced electrodes, a measurement control unit located in proximity to the surface of said earth formation, and a downhole cable having a plurality of first connection lines connected to said downhole tool and said measurement control unit, where the downhole tool includes means for causing said electrodes to contact the inner peripheral surface of said casing, and a plurality of second connection lines with one end connected to a corresponding one of said electrodes and another end connectable to corresponding first connection lines, said method comprising:
 (a) causing said electrodes of said downhole tool to contact said inner casing surface;
 (b) arranging a relay in said tool which is capable of being positioned in first and second positions into a first position such that said first connection lines of said downhole cable are short-circuited, and measuring the potential difference across at least first set of said first connection lines to obtain a first potential difference measurement;
 (c) moving said relay into said second position such that electrical connection between said measurement control unit and said electrodes of said downhole tool is established via said first set of first connection lines and corresponding second connection lines, and measuring the potential difference across at least said first set of said first connection lines to obtain a second potential difference measurement;
 (d) subtracting said first potential difference measurement from said second potential difference measurement to provide a corrected potential difference determination along said casing.

23. A method according to claim 22, further comprising:
 (e) with said relay in said first position, injecting a current into a first first connection line, and measuring the potential difference between said first first connection line and a second first connection line to obtain a third potential difference determination;
 (f) with said relay in said second position, injecting a current into said first first connection line, and measuring the potential difference between said first first connection line and said second first connection line to obtain a fourth potential difference determination;
 (g) determining the contact resistance between the electrodes correspondingly connected to said first and second first connection lines, said contact resistance being determined from said third and fourth potential difference determinations, the corrected potential difference determination obtained at step (d) for the electrodes corresponding to said first and second first connection lines, and said value of said injected current.

24. A method according to claim 23, wherein:
said contact resistance is determined by dividing the difference of said third potential difference determination and said fourth potential difference determination by the value of said injected current, and subtracting therefrom the value of the corrected potential difference determination obtained at step (d) for the electrodes corresponding to said first and second first connection lines divided by said value of said injected current.

25. A method according to claim 23, further comprising:
 (h) setting a threshold contact resistance, wherein said corrected potential difference determination is deemed valid only if said contact resistance determination corresponding to said corrected potential difference determination is below said threshold contact resistance.

26. A method according to claim 22, wherein said downhole tool comprises at least an inner pair and outer pair of electrodes and a second connection line for each electrode, and said cable includes a first connection line for each second connection line, said method further comprising:
 (e) with said relay in said second position, applying a current across said outer electrodes via first and second connection lines associated with said outer electrodes, and measuring the potential difference across the first connection lines connected to said inner electrodes via said second connection lines connected to said inner electrodes and said relay to obtain a third potential difference measurement;
 (f) dividing the difference of said third potential difference measurement and a potential difference measurement across the first connection lines connected to said inner electrodes obtained at step (c) by the value of said applied current to provide a casing resistance determination along said casing.

27. A method according to claim 25, wherein said downhole tool comprises at least an inner pair and outer pair of electrodes and a second connection line for each electrode, and said cable includes a first connection line for each second connection line, said method further comprising:
 (i) with said relay in said second position, applying a second current across said outer electrodes via first and second connection lines associated with said outer electrodes, and measuring the potential difference across the first connection lines connected to said inner electrodes via said second connection lines connected to said inner electrodes and said relay to obtain a fifth potential difference measurement;

(j) dividing the difference of said fifth potential difference measurement and a potential difference measurement across the first connection lines connected to said inner electrodes obtained at step (c) by the value of said applied current to provide a casing resistance determination along said casing, wherein said casing resistance determination is deemed valid only if said contact resistance determination corresponding to said corrected potential difference determination is below said threshold contact resistance.

* * * * *